（12) United States Patent
Papandreou et al.

(10) Patent No.: US 11,621,078 B2
(45) Date of Patent: Apr. 4, 2023

(54) PRE-PROCESSING WHOLE SLIDE IMAGES IN COGNITIVE MEDICAL PIPELINES (71) Applicant: INTERNATIONAL BUSINESS MACHINES CORPORATION, Armonk, NY (US)

(72) Inventors: Nikolaos Papandreou, Thalwil (CH); Sonali Andani, Zurich (CH); Andreea Anghel, Adliswil (CH); Milos Stanisavljevic, Adliswil (CH)

(73) Assignee: International Business Machines Corporation, Armonk, NY (US)

( * ) Notice: Subject to any disclaimer, the term of this patent is extended or adjusted under 35 U.S.C. 154(b) by 480 days.

(21) Appl. No.: 16/822,136

(22) Filed: Mar. 18, 2020

(65) Prior Publication Data
US 2021/0295994 A1    Sep. 23, 2021

(51) Int. Cl.
*G06G 7/58*    (2006.01)
*G16H 50/20*    (2018.01)
(Continued)

(52) U.S. Cl.
CPC ............ *G16H 50/20* (2018.01); *G06N 20/00* (2019.01); *G06T 7/0014* (2013.01); *G16H 30/40* (2018.01);
(Continued)

(58) Field of Classification Search
CPC ........ G16H 50/20; G16H 30/40; G16H 40/67; G06N 20/00; G06N 3/0454; G06N 3/08;
(Continued)

(56) References Cited

U.S. PATENT DOCUMENTS

2010/0329535 A1* 12/2010 Macenko ................. G06T 7/90
382/133
2018/0260609 A1* 9/2018 Georgescu ........... G06V 20/693
(Continued)

FOREIGN PATENT DOCUMENTS

WO    2014181347 A2    11/2014
WO    2017051187 A1    3/2017
(Continued)

OTHER PUBLICATIONS

Bejnordi et al., "Stain specific standardization of whole-slide histopathological images", IEEE Transactions on Medical Imaging, Copyright © 2015 IEEE, pp. 1-12.
(Continued)

*Primary Examiner* — Xin Jia
(74) *Attorney, Agent, or Firm* — L. Jeffrey Kelly (57) ABSTRACT

The invention is notably directed to a computer-implemented method for normalizing medical images, e.g., whole slide images. This method includes steps performed for each image of a first subset of images of a dataset. Actual quantities are estimated for each image, including actual stain vectors and, possibly, robust maximum stain concentrations (typically hematoxylin and eosin stain vectors and concentrations). The actual quantities estimated are assessed by comparing them to reference data based on reference quantities estimated for one or more images of a second subset of images of the dataset, where the second subset of images differ from the first subset of images. The reference quantities include reference stain vectors. For each image, either the actual quantities or the reference quantities for the dataset are selected as effective quantities, based on an outcome of the previous assessment of the actual quantities. Each image is then normalized.

20 Claims, 7 Drawing Sheets

(51) Int. Cl.
G06T 7/00 (2017.01)
G16H 30/40 (2018.01)
G06N 20/00 (2019.01)
G01N 1/30 (2006.01)

(52) U.S. Cl.
CPC ...... *G01N 1/30* (2013.01); *G06T 2207/10056* (2013.01); *G06T 2207/20081* (2013.01); *G06T 2207/20084* (2013.01); *G06T 2207/30004* (2013.01); *G06T 2210/12* (2013.01)

(58) Field of Classification Search
CPC ......... G06T 7/0014; G06T 2207/10056; G06T 2207/20081; G06T 2207/20084; G06T 2207/30004; G06T 2210/12; G06T 2207/10024; G06T 2207/30024; G06T 5/009; G01N 1/30
See application file for complete search history.

(56) References Cited

U.S. PATENT DOCUMENTS

2019/0130570 A1* 5/2019 Jackson ................ G06T 7/0014
2019/0355113 A1* 11/2019 Wirch ................ G06F 3/04845

FOREIGN PATENT DOCUMENTS

WO 2019025515 A1 2/2019
WO WO-2019025533 A1 * 2/2019 ......... G01N 15/1475

OTHER PUBLICATIONS

Grace Period Disclosure, Anghel et al., "A High-Performance System for Robust Stain Normalization of Whole-Slide Images in Histopathology", frontiers, Published online Sep. 30, 2019, 14 pages.
Macenko et al., "A Method for Normalizing Histology Slides for Quantitative Analysis", © 2009 IEEE, ISBI 2009, pp. 1107-1110.
Ruifrok et al., "Quantification of Histochemical Staining by Color Deconvolution", Analytical and Quantitative Cytology and Histology, Analyt Quant Cytol Histol 2001, 23:291-299.
Stanisavljevic et al., "A Fast and Scalable Pipeline for Stain Normalization of Whole-Slide Images in Histopathology", ECCV 2018 workshop paper, 14 pages.
Vahadane et al., "Structure-Preserving Color Normalization and Sparse Stain Separation for Histological Images", IEEE Transactions on Medical Imaging, vol. 35, No. 8, Aug. 2016, pp. 1962-1971.
Mell et al., "The NIST Definition of Cloud Computing", Recommendations of the National Institute of Standards and Technology, Special Publication 800-145, Sep. 2011, 7 pages.

* cited by examiner

PRE-PROCESSING WHOLE SLIDE IMAGES IN COGNITIVE MEDICAL PIPELINES

STATEMENT REGARDING PRIOR DISCLOSURES BY THE INVENTOR OR A JOINT INVENTOR

Aspects of the present invention may have been disclosed by the inventor, or a joint inventor, in the publication "frontiers in Medicine: Pathology", all made available to the public on Sep. 30, 2019. These aspects, as they may appear in the claims, may be subject to consideration under 35 U.S.C. § 102(b)(1)(A).

BACKGROUND

The invention relates in general to the field of computer-implemented methods for normalizing medical images such as used in computer-aided diagnosis (CAD) and, in particular, in digital pathology, as well as related computer systems, and computer program products. In particular, it is directed to methods for accelerating the preprocessing of whole slide images for cognitive medical pipelines using machine learning (ML).

A whole slide image (WSI), also called a "virtual slide", is a digitized histopathology glass slide that has been obtained on a slide scanner. A digitized slide depicts a high-resolution replica of the original glass. It can be manipulated through software to emulate microscope review and diagnosis. A WSI emulates conventional light microscopy with the help of hardware and computerized processes. Such processes involve specialized hardware (the slide scanner) to digitize the glass slides, which causes to generate a very large digital image (the WSI). Software is then used to view and/or analyze the digital files.

With the advent of high-resolution whole-slide imaging technology and advances in deep learning, CAD systems have become an important part of the clinical work today. ML-based image analysis algorithms applied to digitized histological slides can assist pathologists in terms of workload reduction, efficient decision support and interpretability of the results. Given the vast amount of gigapixel-sized WSI data and the need to accelerate the time-to-insight, there is a need to achieve automated and scalable pipelines for large-scale, fast, and robust image analysis.

Stain normalization is an important process of the analysis pipeline in many histology image processing algorithms. The goal of stain normalization is to reduce the variability between different images by estimating the stain colors, and in particular the concentrations of each stain in each pixel of the image, and subsequently normalizing the stain intensity vectors in accordance to a template. A reliable stain color estimation (or deconvolution) process is therefore required. The stain deconvolution process transforms a stained tissue section image from the RGB color space into a series of stain channels, where each stain channel represents the intensity of a particular stain expression across the original image. The RGB color space is a color model in which red, green, and blue light are added together in differing amounts to produce a broad array of colors.

Despite standardized staining protocols, variations in the staining results are still frequent due to differences in, e.g., the antigen concentration and incubation time and temperature, the different conditions across slide scanners, etc. Such color/intensity variations, in particular among images from different hospitals, can adversely affect the performance and accuracy of the CAD systems. There, a stain normalization method can help the CAD systems by generating images with a standardized appearance of the different stains.

For example, a high-performance stain normalization method was proposed in Macenko M, Niethammer M, Marron J S, Borland D, Woosley J T, Guan X, et al. ("A method for normalizing histology slides for actual quantitative analysis", 2009 IEEE International Symposium on Biomedical Imaging (2009), 1107-1110), hereafter referred to as reference [1]. This method estimates the stain vectors of the WSI of interest by using a singular value decomposition approach applied to the non-background pixels of the input image. However, this approach fails to suitably normalize images containing artifacts.

SUMMARY

According to a first aspect, the present invention is embodied as a computer-implemented method for normalizing medical images, e.g., whole slide images. This method includes a number of steps, which are performed for each image of a first subset of images of a dataset. First, actual quantities are estimated for each image. The actual quantities include actual stain vectors and, possibly, stain concentrations (typically hematoxylin and eosin stain vectors and concentrations). Then, the actual quantities estimated are assessed by comparing them to reference data. The latter are based on reference quantities estimated for one or more images of a second subset of images of the dataset, where the second subset of images differ from the first subset of images. The reference quantities also include reference stain vectors. Next, the method proceeds to select, for each image, either the actual quantities or the reference quantities for the dataset as effective quantities, based on an outcome of the previous assessment of the actual quantities. Finally, each image is normalized, based on the effective quantities previously selected, in order to obtain a normalized image.

The reference data may for example be precomputed. In variants, they are automatically updated as images of the dataset are processed. In embodiments, the method further maintains metadata for the dataset of images. Such metadata are accessed to decide whether to skip steps of estimating actual quantities and assessing such quantities for images of a third subset of the dataset. If such steps happen to be skipped, then the reference quantities are automatically selected as effective quantities for normalizing such images.

According to another aspect, the invention is embodied as a computerized system for normalizing medical images. The system includes storage means storing instructions and a dataset of images, and processing means. The latter are configured to execute the instructions, to cause the system to perform steps such as described above, i.e., for each image of a first subset of images of the dataset, actual quantities (including actual stain vectors) are estimated for each image. They are then assessed by comparing them to reference data. The latter are based on reference quantities estimated for one or more images of a second subset of images, which differ from the first subset of images. The reference quantities include reference stain vectors. Then, based on an outcome of assessing the actual quantities, the system selects either the actual quantities or the reference quantities as effective quantities. It finally normalizes each image, based on the effective quantities selected, to obtain a normalized image.

According to a final aspect, the invention is embodied as a computer program product for normalizing medical images. The computer program product includes a computer readable storage medium having program instructions embodied therewith. The program instructions are executable by one or more processors, to cause to implement steps according to the present methods.

Computerized systems, methods, and computer program products embodying the present invention will now be described, by way of non-limiting examples, and in reference to the accompanying drawings.

BRIEF DESCRIPTION OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which:

FIG. 1 further shows a data flow between such components, as involved in embodiments;

FIG. 7 depicts abstraction model layers according to an embodiment of the present invention. The accompanying drawings show simplified representations of the systems or components thereof. Similar or functionally similar elements in the figures have been allocated the same numeral references, unless otherwise indicated.

DETAILED DESCRIPTION

The following description is structured as follows. General embodiments and high-level variants are described in section 1. Section 2 addresses more specific embodiments and technical implementation details.

1. General Embodiments and High-Level Variants

Figure 1:
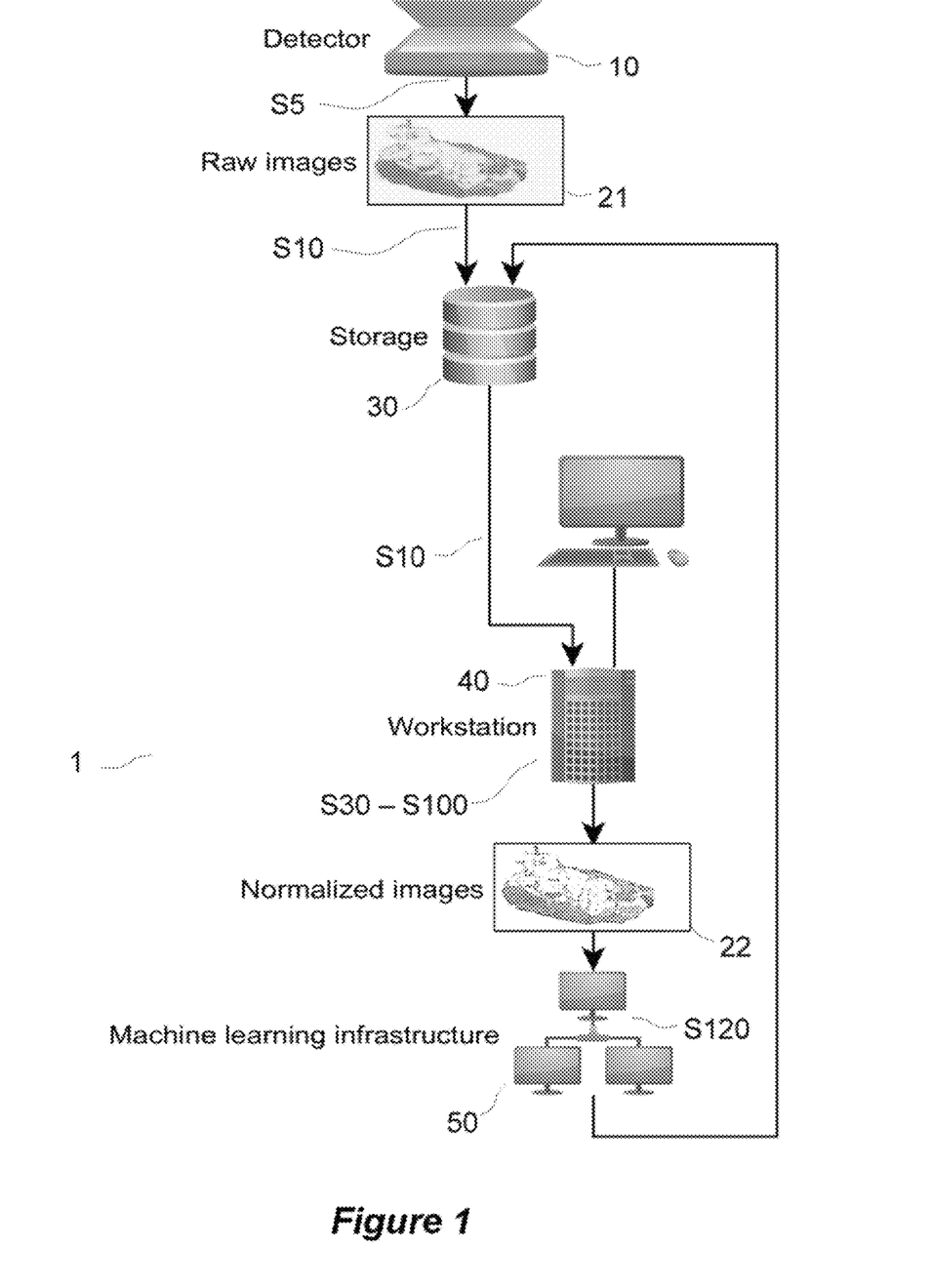
FIG. 1 schematically represents components of a computer-aided diagnosis (CAD) system for digital pathology, suited for implementing method steps according to embodiments of the invention.
Figure 2:
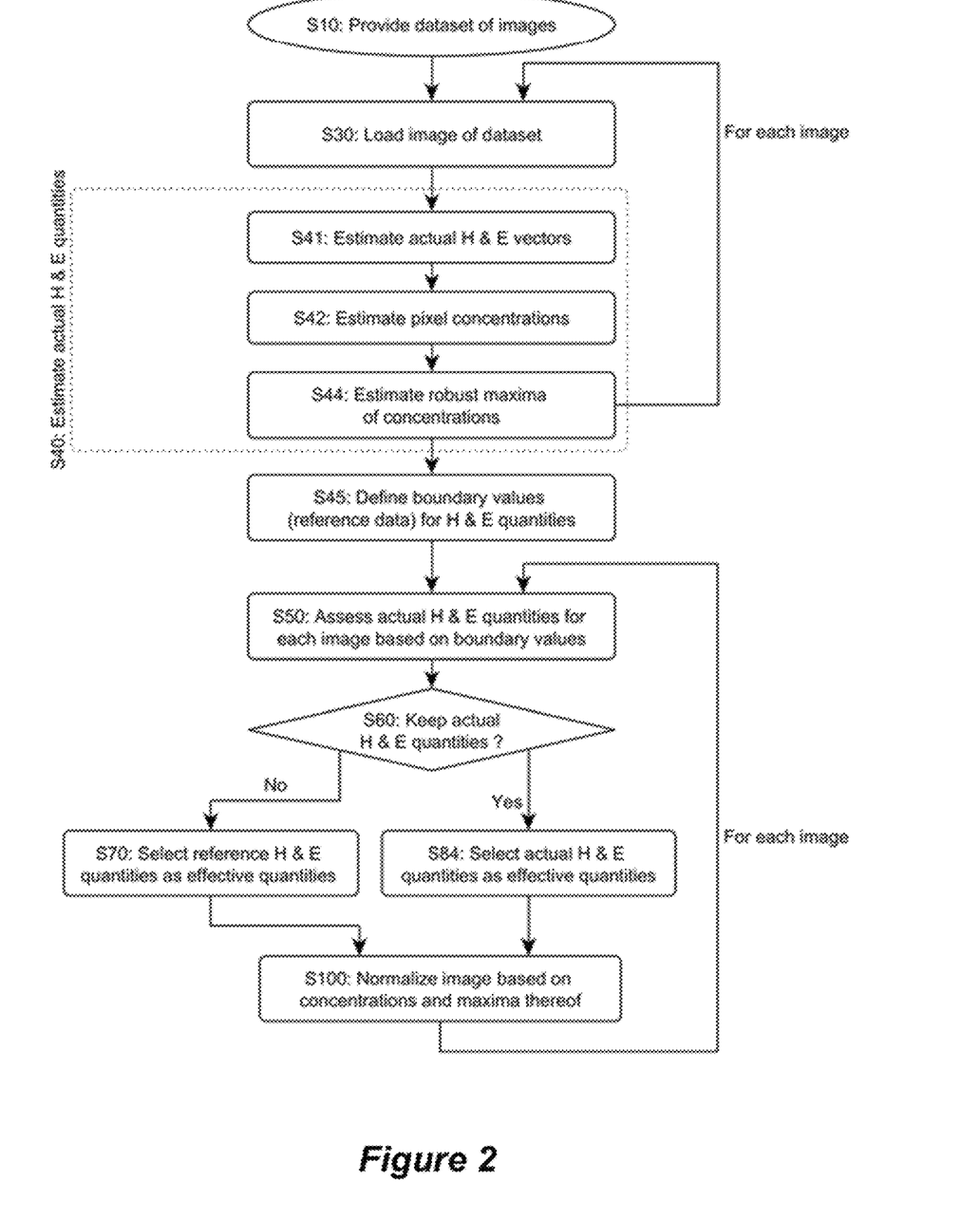
FIGS. 2 and 3 are flowcharts illustrating high-level steps of two different methods for normalizing medical images, each according to embodiments.
Figure 3:
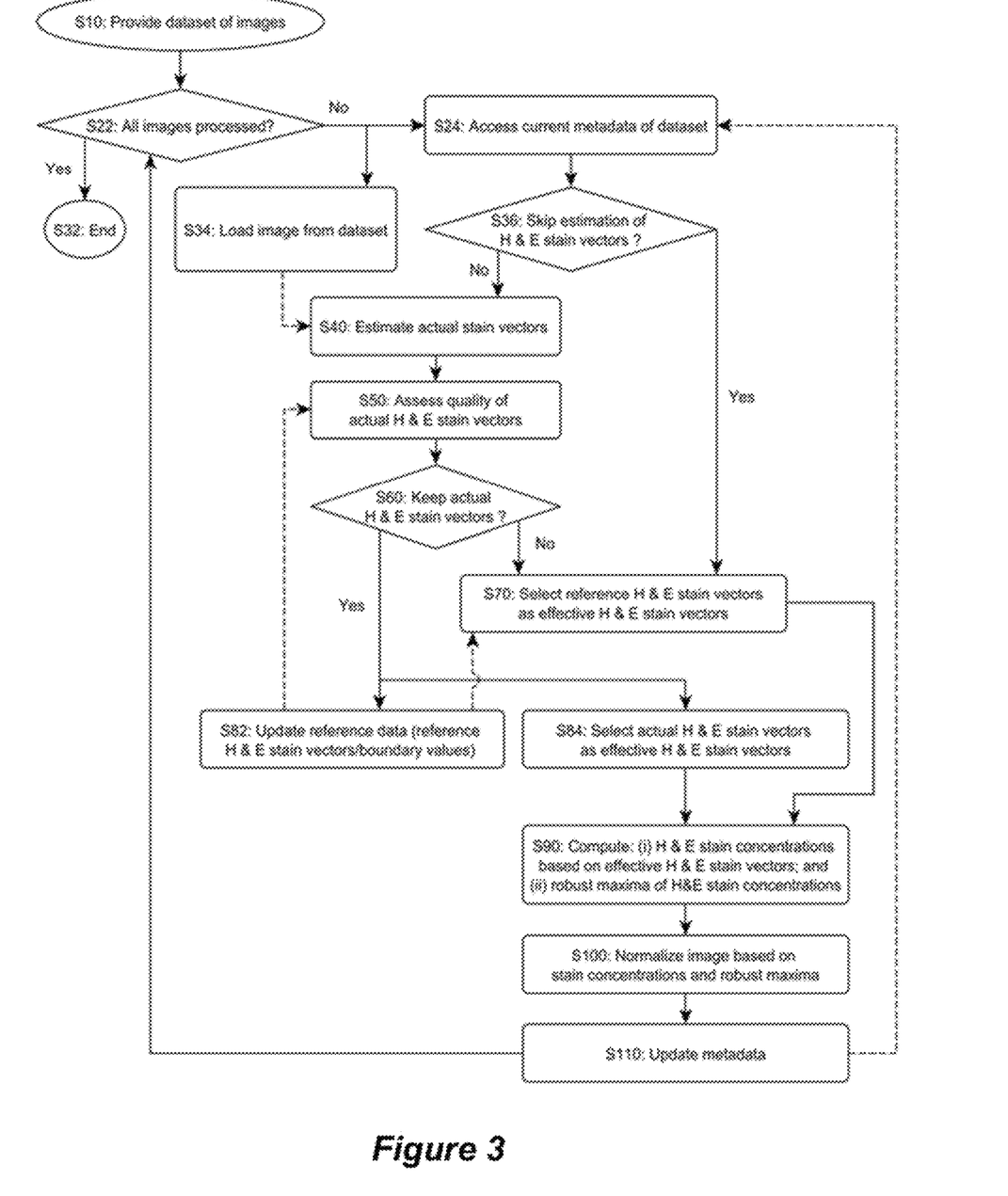

In reference to FIGS. 1-3, an aspect of the invention is first described, which concerns a computer-implemented method for normalizing medical images, e.g., whole slide images (WSIs) as obtained with a slide scanner. Various embodiments of this method can be contemplated. FIGS. 2 and 3 are flowcharts reflecting two preferred embodiments, where references "Sij" refer to method steps. This method and its variants are collectively referred to as the "present methods" in this document. The present methods are typically implemented in a system 1 such as depicted in FIG. 1. Such methods aim at improving the normalization of medical images, and possibly speed up the time required to normalize them. These methods can advantageously be used in a cognitive medial pipeline, as described later in detail.

Essentially, such methods include the following steps, which are performed for each image 21 of a first subset of images of a dataset. First, actual quantities are estimated (step S40) for each image 21 of the first subset. These quantities include actual stain vectors, typically hematoxylin and eosin (H & E) vectors, see step S41. They may possibly include maximum stain concentrations (e.g., maximum H & E concentrations), step S44, where the maximum stain concentrations are computed from pixel concentrations, step S42, which are themselves computed from the actual stain vectors, as discussed later in detail.

Then, the actual quantities as estimated at step S40 are assessed at step S50. The aim is to assess the quality of the actual quantities estimated for each image 21. This assessment is performed by comparing the actual quantities to some reference data. The latter are based on reference quantities, where the reference quantities are quantities that are (or have already been) estimated for one or more images of a second subset of images of the dataset. The reference quantities include stain vectors (called reference stain vectors) and may possibly include maximum stain concentrations too (called reference maximum stain concentrations). And again, the reference quantities are typically H & E quantities, i.e., H & E vectors and, possibly, maximum H & E concentrations. In the following, H & E quantities are assumed, for the sake of illustration. However, it will be apparent to the one skilled in the art that the present methods equally apply to other stain coloring procedures.

The second subset of images typically include or consist of one or more good-quality images. A single image may suffice to obtain the reference quantities needed. More generally though, the second subset may possibly include several images, which are preferably selected to provide the best possible quality. Such images are chosen as reference images for the purpose of obtaining reference data for the particular dataset of images. The first subset of images includes remaining images that need to be processed for normalization and may possibly be much larger than the second subset. Images of the first subset may be of lesser quality than images of the second subset. In particular, the first subset of images may contain images that have artifacts, e.g., stain spots, dirt, etc.; those images are referred to as poor-quality images. However, the first subset of images may contain good-quality images too (possibly many of them), in addition to poor-quality images. The second subset of images thus differ from the first subset of images; there will normally be no overlap between images of the two subsets. Importantly, such subsets are not necessarily defined beforehand (though they can be, by first selecting good-quality images). Indeed, the present methods may update the reference data as images are processed (e.g., one by one or in parallel), as discussed later in detail.

Next, each image of the first subset is associated to either the actual quantities as estimated for this image or the reference quantities for the dataset. That is, the method either selects the actual quantities (step S84) or the reference quantities (step S70) as effective quantities for each image. The selection depends, step S60 on the outcome of the quality assessment of the actual quantities made at step S50. This allows distorted H & E quantities of images in the first subset to be replaced by more suitable H & E quantities.

Finally, each image 21 is normalized, step S100, based on the effective quantities previously selected at steps S70, S84. This makes it possible to obtain improved normalized versions 22 of the images 21, where the normalization relies either on the actual stain vectors or the reference stain vectors, depending on the quality of the H & E quantities obtained for such images.

The normalization step S100 typically requires H & E stain concentrations, which can be computed as part of the computation S40 of actual quantities of the images 21 (as assumed in FIG. 2) or in a subsequent step S90 (as assumed in FIG. 3), depending on whether the quantities selected for the estimation and assessment steps S40, S50 contain the maximum stain concentrations, or not.

The methods proposed herein allow problematic estimations for input images 21 to be automatically detected, thanks to the systematic assessment S50 based on H & E quantities. If problematic quantities are detected, the method substitutes them with reference H & E quantities (that include H & E vectors) to normalize the images. That is, the reference H & E quantities are used as representative H & E quantities for the dataset, where the reference quantities are typically obtained from a subset of good-quality images (i.e., free or substantially free of artifacts).

A key advantage of the proposed method is to alleviate normalization errors that would else occur in the presence of artifacts. Indeed, the assessment, step S50, performed allows artifacts to be implicitly detected, by comparing actual H & E quantities to the reference H & E quantities obtained. As such artifacts impact the actual H & E quantities and, in turn, the normalization, step S100, better normalization results can be achieved using the reference H & E quantities, where needed. This approach proves to be effective in practice as images 21 from a same dataset are normally subjected to a similar staining process.

In that respect, the present methods may further impose to use, step S10, images obtained from a same staining process (i.e., a staining process following a same protocol for each image of the dataset), as in embodiments. Incidentally, the present methods may further include a preliminary step of obtaining, step S5, the images, e.g., thanks to a slide scanner 10 (or more generally a detector), and according to a same staining process, as assumed in FIG. 1.

In variants to the present solution, one may for instance contemplate to compute a RGB histogram of each image 21, in order to identify the presence of artifacts, and then filter out image portions that correspond to the identified artifacts, prior to normalizing the images. However, such an approach would only work if the color space of the artifacts does not overlap with that of the useful pixels. On the contrary, it can be realized that the present methods also work where the color space of the artifacts overlaps with that of the useful pixels, hence an additional advantage of the present approach.

All this is now described in detail, in reference to particular embodiments of the invention. To start with, the actual quantities estimated at S40 may possibly include maximum stain concentrations, e.g., maximum H & E concentrations (see step S44), as assumed in the flowchart of FIG. 2. Similarly, the reference quantities may also include reference maximum stain concentrations. In variants, the assessment of the actual H & E quantities can be based on the sole stain vectors (actual) as estimated for each image 21 of the first subset (i.e., by comparing actual vectors to reference vectors, without comparing maximum concentrations). In that case, stain concentrations and their corresponding maximum values can be computed, step S90, subsequently, in view of normalizing, step S100, the images, as assumed in FIG. 3. In both cases, each image 21 is preferably normalized, step S100, based on both the stain concentrations stemming from the effective vectors selected and the maximum stain concentrations computed according to such concentrations.

Note, the values of the components of the stain vectors are typically computed based on color information from all pixels. Such vector components refer to certain colors, e.g., red (R), green (G), and blue (B), as in embodiments. Thus, H & E vectors give rise to six components per image in that case: three RGB components for hematoxylin and three RGB components for eosin. Then, the stain concentrations can be computed (for each pixel) based on the effective stain vectors retained for each image 21 and the corresponding maximum stain concentrations can be determined, e.g., as robust maxima.

Figure 4:
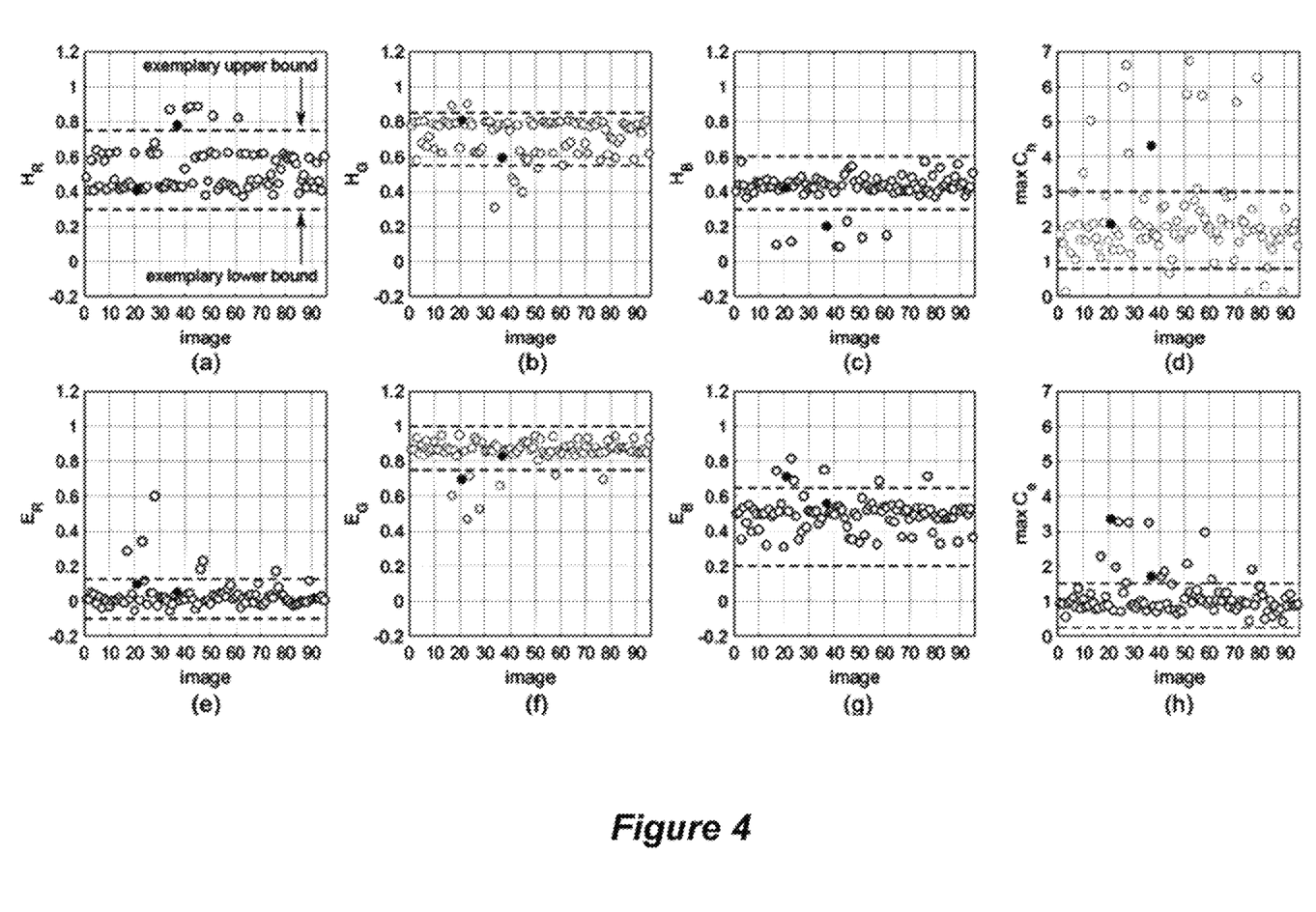
FIG. 4 aggregates various plots representing hematoxylin and eosin (H & E) vectors, and maximum H & E stain concentrations as obtained for a given dataset of whole slide images, represented as dots or circles. The plots further illustrate how such H & E quantities can be used to define two subsets of images (i.e., good-quality images and bad-quality images), based on boundary values, as in embodiments.

Now referring to FIG. 4, FIG. 4 aggregates various plots representing hematoxylin and eosin (H & E) vectors, and maximum H & E stain concentrations as obtained for a given dataset of whole slide images, represented as dots or circles. The plots further illustrate how such H & E quantities can be used to define two subsets of images (i.e., good-quality images and bad-quality images), based on boundary values, as in embodiments.

There are two components of maximum concentrations per image, referred to as max $C_h$ and max $C_e$ in FIG. 4 (see FIGS. 4(d) and 4(h)), while there are 2 N components of pixel stain concentrations $C_h$ and $C_e$ per images, N being the number of pixels per image.

That is, in preferred embodiments, the maximum stain concentrations (computed as part of the actual quantities and the reference quantities) are preferably computed at steps S40, S90, based on effective stain vectors, as robust maxima of pixel stain concentrations $C_h$ and $C_e$ in the corresponding images. Such concentrations may for instance correspond to a given percentile, e.g., the 99th percentile. Thus, the stain normalization scheme may use both the H & E vectors and the robust maximum concentrations of the two stains.

In preferred embodiments, the method computes the following quantities for each image of the first subset. First, actual H & E vectors (6 components in total) are computed. Second, actual pixel stain concentrations (2 N components in total) are obtained based on the actual vectors computed. Third, actual maximum concentrations (2 components) are computed based on the actual pixel stain concentrations. Then the actual H & E vectors are compared to reference vectors (as obtained from reference images, i.e., images of the second subset) and the actual maximum concentrations are compared to the reference maximum concentrations. Based on this comparison, effective quantities are selected, which include both the H & E vectors and the maximum concentrations. Finally, depending on the effective vectors selected for each image of the first subset, the pixel stain concentrations may have to be recomputed. I.e., the pixel stain concentrations may need be recomputed based on the reference vectors if the comparison results in selecting the reference quantities rather than the actual quantities. The effective pixel stain concentrations accordingly obtained (i.e., either the actual concentrations or the concentration re-evaluated based on the reference vectors, depending on comparison) are then used, together with the effective maximum concentrations (either taken as then reference maxima or obtained based on the re-evaluated pixel concentrations), for normalization purposes. Note, the effective maximum concentrations used for normalization can be obtained based on the re-evaluated pixel concentrations (where necessary). Still, one may instead use as effective maximum concentrations the maximum concentrations as initially determined from the reference vectors, without it being needed to recompute the maximum concentrations based on the new effective concentrations.

In each of the embodiments of FIGS. 2 and 3, the reference quantities are estimated at step S40 for each image of the second subset, it being noted that, for the reference images (i.e., images of the second subset), the "reference quantities" are intrinsically "actual quantities" as estimated for such images. Next, the reference data are obtained at steps S45, S82 based on the reference quantities as estimated at step S40. The reference data may notably be obtained during a single, preliminary step S45 (in FIG. 2) or may be progressively updated at step S82 (in FIG. 3) as images of the dataset are processed, if necessary. In both cases, such reference data may for example be obtained as boundary values of actual quantities, as illustrated by way of dashed lines in FIG. 5, as described in further detail in Section 2.

As evoked earlier, a single reference image may possibly be selected as a reference for the whole dataset. More generally, several images can be used as references. For example, for each new dataset, one may choose one or more WSIs of high quality, based on the corresponding H & E quantities, and then select such quantities as reference H & E quantities for remaining images of the dataset. All remaining images can then be normalized based on reference H & E quantities accordingly selected.

In the example of FIG. 2, the reference quantities are estimated, step S40, for all images of the dataset (after having loaded such images at step S30), prior to assessing, step S50, such quantities, and in view of selecting, steps S60, S70, S84, the effective H & E quantities for the images. Reference H & E quantities correspond to good-quality images, while actual H & E quantities of bad-quality images are replaced by reference H & E quantities, in view of the normalization step S100. In variants, the reference quantities are estimated based on several, good-quality images forming a subset (called second subset) of the images. This subset is defined either by manually selecting one or more good-quality images from the dataset or after having estimated H & E quantities of all images of the dataset and determined good-quality images of the dataset, e.g., by assessing distance-based metrics as described below. In other variants, the second subset of images is progressively defined; it progressively grows as the method proceeds and additional, good-quality images are identified, as in FIG. 3.

The assessment performed at step S50 can, for instance, be made by comparing actual H & E quantities (e.g., by computing suitable distance metrics) to a predefined, ideal set of H & E quantities, for example. In preferred variants, however, this assessment step S50 is based on boundary values, e.g., defined, at step S45, based on all actual H & E quantities as estimated, step S40, for all images of the dataset, as assumed in FIG. 2. Boundary values allows subsets of good-quality images and bad-quality images to be easily defined.

Boundary values can also be used in the example of FIG. 3, where they can be progressively refined, as images are processed, one after the other. That is, one may first identify a good-quality image and then process all remaining images, one after the other (as assumed in FIG. 3). There, some of these images may, based on the H & E quantities estimated therefore, be considered bad-quality or good-quality images. If an image is considered a good-quality image, it may then be beneficial to update, step S82, the pool of reference H & E quantities, as illustrated in FIG. 3. Thus, the algorithm may incrementally update the reference data, based on H & E quantities obtained for the good-quality images. In passing, one understands that the steps of the present methods may be executed in different possible orders or be intertwined. E.g., one may first compute all actual quantities and then assess them prior to normalizing images, or one may first compute quantities pertaining to a single, good-quality images (visually determined) and then successively process all remaining images and incrementally update the reference data, if needed.

For instance, in FIG. 3, the method may process each image 21 of the dataset and update the reference data conditional on the quality of the actual H & E quantities as estimated for each successive image of the dataset. As an example, consider three images of the dataset. After assessing, step S50, the stain vectors as estimated, step S40, for the first image using any suitable, initial reference data, the reference data may possibly be update, step S82, based on the stain vectors as estimated, step S40, for the first image (if such stain vectors happen to match some quality criteria). Then, after assessing, step S50, the stain vectors as estimated, step S40, for the second image, the reference data may be updated, step S82, based on the stain vectors as estimated for both the first image and the second image. There, the stain vectors as estimated, step S40, for the third image can be assessed, step S50, by comparing them to reference data updated based on the two sets of stain vectors as respectively estimated for the first image and the second image, and so on, as illustrated in FIG. 3.

In variants to boundary values, the actual quantities are assessed S50 by measuring distances between the actual stain vectors and the reference stain vectors (again, maximum stain concentration may be considered too). Such "distances" should be understood in a broad sense. I.e., any suitable metric (e.g., Euclidian distances) can be used. Next, the actual quantities can for instance be assessed S50 by comparing the measured distance to a threshold distance. The algorithm may notably select S70 the reference stain vectors if the distance happens to be larger than a given threshold distance, for example.

Preferred, however, is to use boundary values, as discussed earlier. Nevertheless, it can be noted that using boundary values or comparing distances eventually amounts to comparing actual values to reference values, albeit using different metrics. One may, for example, consider the mean or median values of all actual H & E vectors and select only those quantities that remain within allowed boundary values (e.g., ±20% from the mean vector value), as obtained based on all good-quality images of a same dataset. And again, the H & E quantities may include maximum stain concentrations. In fact, the H & E quantities considered preferably consist of the stain vectors and the maximum stain concentrations.

Where reference data are computed, steps S45, S82, as boundary values, the actual quantities are assessed, step S50, by verifying whether values of the actual quantities estimated for each image 21 lie outside of domains bounded by the boundary values. If such values are verified, step S50, to lie outside of the domains, then the reference quantities are selected, step S70, as effective quantities for each image 21. E.g., if any image has at least one outlier value, this image is considered as a poor-quality image.

This is illustrated in FIG. 4, which shows H & E vector values and maximum concentration values $C_h$ and $C_e$ (represented as dots), for various image identifiers, as usual. The black dots denote the presence of artifacts. In detail, for all images in a dataset, a method as discussed above is performed to extract, step S40, the H & E vectors of the three RGB channels, see FIGS. 4(a)-4(c), 4(e)-4(g), and the maximum $C_h$ and $C_e$ stain concentration values, see FIGS. 4(d), 4(h). Next, acceptable ranges are defined for the values of each H & E channel and maximum concentrations $C_h$ and $C_e$. FIG. 4(a) shows an example of such a range defined by a lower bound and an upper bound. A value that falls outside its respective range is considered an outlier and any image that has at least one outlier value is considered of poor quality.

Otherwise, the image is considered a good-quality image. Once poor-quality mages have been identified, they can be normalized by using the reference set of H & E vector values and maximum $C_h$ and $C_e$ stain concentration values. This reference set is derived from the values of the good-quality images from the same dataset, by taking the mean of $H_R$, $H_G$, $H_B$, $E_R$, $E_G$, $E_B$, maximum $C_h$ and maximum $C_e$, respectively.

In further embodiments, the estimation of actual H & E quantities may even be skipped for a residual subset (call it a third subset) of the images, as illustrated in FIG. 3. Namely, metadata of the dataset may be updated, step S110, as images are processed, based on outcomes of steps of assessing, step S50, the actual quantities as estimated, step S40, for each image 21 (based on loaded images at step S34). Such metadata may for example aggregate statistics as to whether actual quantities as estimated at step S40 for the images of the dataset have been selected, step S84, as effective quantities or not, step S70. Then, after loading, step S24, such metadata, if the metadata indicates that actual H & E quantities are mostly discarded, the algorithm may simply decide, step S36, to skip steps of estimating actual quantities and assessing actual quantities for all remaining images of the dataset. In that case, the reference quantities are selected, step S70, by default as effective quantities for normalizing, step S100, all remaining images of the third subset. The process is performed, step S22, for all images of interest and then stopped, step S32.

For example, if the latest metadata loaded, step S24, indicates that less than a given percentage (e.g., less than 30%) of the vectors estimated for images of the dataset are eventually selected as effective vectors for such images, then it may systematically be relied on the reference vectors for all subsequent images of the dataset, to speed up the normalization process.

Eventually, the normalized images may possibly be subject to a cognitive treatment, as in embodiments, where a cognitive algorithm is run, step S120, on normalized images obtained from one or more datasets of image. The cognitive algorithm may for example be run is an unsupervised way, e.g., to estimate distance between images. In variants, the cognitive algorithm is a supervised learning algorithm. In both cases, the normalization schemes adopted here benefit to the accuracy of the machine learning (ML) pipeline.

For example, one may employ a convolutional neural network (CNN) model. The latter is trained on images normalized using H & E vectors and maximum $C_h$ and $C_e$ values, selected, steps S70, S84, as part of effective quantities retained for the images. This way, the outliers, i.e., poor-quality images, are normalized using the reference vectors and maximum concentrations of the good-quality images. Tests performed by the inventors have shown that such a model better generalizes on an unseen (test) dataset.

The above embodiments have been succinctly described in reference to the accompanying drawings and may accommodate a number of variants. Several combinations of the above features may be contemplated. Examples are given in section 2.1.

Figure 5:
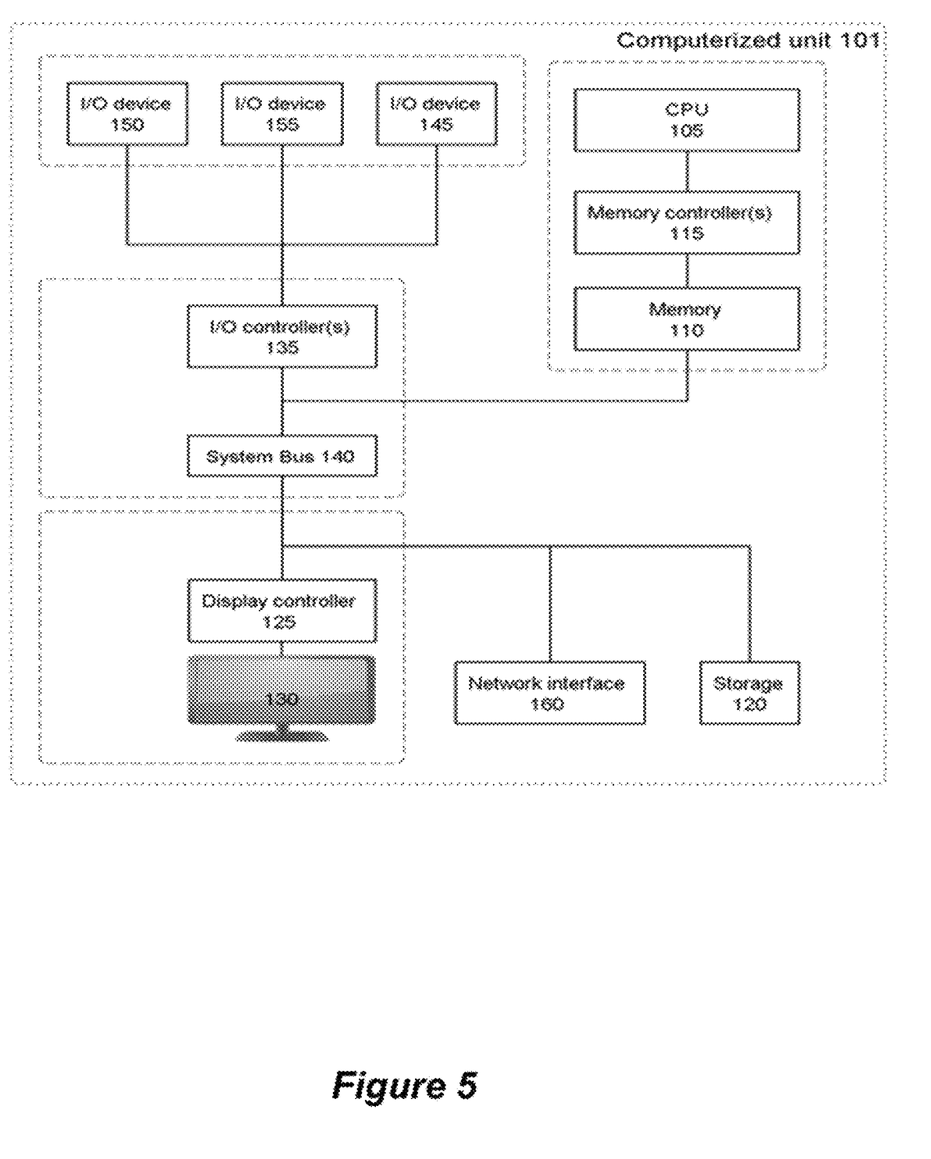
FIG. 5 schematically represents a general-purpose computerized unit that may be involved in a computerized system according to embodiments, possibly in several places of this system, and suited for implementing one or more steps of methods according to embodiments of the invention.

Referring to FIGS. 1 and 5, another aspect of the invention is now described, which concerns a computerized system 1 for normalizing medical images. An example of such a system is depicted in FIG. 1. Basically, the system includes storage means 30, 40, 120, which may be distributed across several interconnected machines, as assumed in FIG. 1. Such storage means notably store instructions and one or more datasets of images 21. The system further includes processing means 105 configured to execute the instructions, to perform steps as described earlier in reference to FIGS. 1-3.

The system may notably be configured as a digital pathology system 1, i.e., an image-based computer system that enables the acquisition, management and interpretation of pathology information generated from a digitized glass slide. The system may further include a scanner 10 itself, or, more generally, any kind of detector from which images are generated.

In the example of FIG. 1, the system includes the slide scanner 10, which is used to obtain images 21. The latter are stored on the storage means 30, prior to being processed by a workstation 40, in order to be normalized. The workstation 40 is connected, e.g., to a cloud 50, where nodes cooperate to train a cognitive model based on normalized images 22. More generally, the ML infrastructure 50 may be separate from the workstation 40. In variants, both the normalization procedure and the learning are performed at a same machine. Each of the storage unit 30, the workstation 40, and the nodes of the infrastructure 50 may include one or more computerized unit 101 such as shown in FIG. 5. Such a unit 101 is discussed in detail in section 2.2.

According to a final aspect, the invention can be embodied as a computer program product for normalizing medical images. Generally speaking, the computer program product includes one or more computer readable storage media having program instructions embodied therewith. Such program instructions are executable by one or more processors, e.g., of the units 30, 40, 50 of the system shown in FIG. 1, in order to cause to perform steps according to the present methods. Additional details concerning such computer program products are discussed in section 2.3.

2. Specific Embodiments—Technical Implementation Details 2.1 Specific Embodiments Particularly preferred embodiments build on the Macenko's normalization method [1] to achieve a high-performance stain normalization system 1 for WSIs. This method estimates the stain vectors of WSIs of interest by using a singular value decomposition (SVD) approach applied to the sole non-background pixels of each input image 21. The simplicity of the algorithmic steps of this method makes prone to efficient parallelization. The normalization procedure does not involve intermediate training steps of a cognitive model and is thus tractable, computationally speaking.

A preferred stain normalization system architecture is based on an optimized multi-core implementation that integrates multiple system-level optimizations. The latter mitigate issues in terms of processing times and system memory consumption, when normalizing high-resolution images. As a result, and contrary to typical implementations of stain normalization algorithms, the preferred implementation can process high-resolution images, such as 40× resolution of a 160 k×80 k WSI corresponding to 37.5 GB of data, on typical servers with less than 64 GB of RAM. This implementation enables the processing of such images and can be used with different image formats, such as .svs, .tif, .ndpi, etc. This allows the performance of the stain normalization system to be evaluated on datasets generated by different scanners.

Furthermore, as the original stain normalization algorithm [1] is sensitive to the quality of the input images, the algorithm implements a method according to present invention to detect poor-quality images and normalize such images, despite the presence of artifacts, as described in detail in section 1. The obtained normalization method can increase the accuracy of ML pipelines that use stain-normalized images as input. As an exemplary pipeline, a CNN was successfully used to detect tumor in prostate biopsy WSIs. Before feeding the ML engine with histological WSIs, the full images are normalized in a user pre-defined resolution, e.g., 10×. The normalized images can be stored to disk or directly pipelined with the ML engine. Then, the latter trains a CNN model using patches from the normalized WSI. The trained model is then used for inference to predict the presence of tumor in images.

2.2 Computerized Units

Computerized devices can be suitably designed for implementing embodiments of the present invention as described herein. In that respect, it can be appreciated that the methods described herein are largely non-interactive and automated. In exemplary embodiments, the methods described herein can be implemented either in an interactive, partly-interactive or non-interactive system. The methods described herein can be implemented in software (e.g., firmware), hardware, or a combination thereof. In exemplary embodiments, the methods described herein are implemented in software, as an executable program, the latter executed by suitable digital processing devices. More generally, embodiments of the present invention can be implemented where general-purpose digital computers, such as personal computers, workstations, etc., are used.

For instance, the computerized unit 101 depicted in FIG. 5 may be a general-purpose computer, which may be used in each of the units 30, 40, 50 of FIG. 1. In exemplary embodiments, in terms of hardware architecture, as shown in FIG. 5, the unit 101 includes a processor 105, memory 110 coupled to a memory controller 115, and one or more input and/or output (I/O) devices 145, 150, 155 (or peripherals) that are communicatively coupled via a local input/output controller 135. The input/output controller 135 can be, but is not limited to, one or more buses or other wired or wireless connections, as is known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 105 is a hardware device for executing software, particularly that stored in memory 110. The processor 105 can be any custom made or commercially available processor, a central processing unit (CPU), an auxiliary processor among several processors associated with the computer 101, a semiconductor-based microprocessor (in the form of a microchip or chip set), or generally any device for executing software instructions.

The memory 110 can include any one or combination of volatile memory elements (e.g., random access memory) and nonvolatile memory elements. Moreover, the memory 110 may incorporate electronic, magnetic, optical, and/or other types of storage media. Note that the memory 110 can have a distributed architecture, where various components are situated remote from one another, but can be accessed by the processor 105.

The software in memory 110 may include one or more separate programs, each of which includes an ordered listing of executable instructions for implementing logical functions. In the example of FIG. 5, the software in the memory 110 includes methods described herein in accordance with exemplary embodiments and a suitable operating system (OS) 111. The OS 111 essentially controls the execution of other computer programs and provides scheduling, input-output control, file and data management, memory management, and communication control and related services.

The methods described herein may be in the form of a source program, executable program (object code), script, or any other entity comprising a set of instructions to be performed. When in a source program form, then the program needs to be translated via a compiler, assembler, interpreter, or the like, as known per se, which may or may not be included within the memory 110, to operate properly in connection with the OS 111. Furthermore, the methods can be written as an object-oriented programming language, which has classes of data and methods, or a procedure programming language, which has routines, subroutines, and/or functions.

Possibly, a conventional keyboard 150 and mouse 155 can be coupled to the input/output controller 135 and other components via a system bus 140. Other I/O devices 145-155 may include other hardware devices. In addition, the I/O devices 145-155 may further include devices that communicate both inputs and outputs. The system 100 can further include a display controller 125 coupled to a display 130. In exemplary embodiments, the system 100 can further include a network interface or transceiver 160 for coupling to a network (not shown) and hence to other similar units 101.

The network transmits and receives data between the unit 101 and external systems. The network is possibly implemented in a wireless fashion, e.g., using wireless protocols and technologies, such as WiFi, WiMax, etc. The network may be a fixed wireless network, a wireless local area network (LAN), a wireless wide area network (WAN) a personal area network (PAN), a virtual private network (VPN), intranet or other suitable network system and includes equipment for receiving and transmitting signals.

The network can also be an IP-based network for communication between the unit 101 and any external server, client and the like via a broadband connection. In exemplary embodiments, network can be a managed IP network administered by a service provider. Besides, the network can be a packet-switched network such as a LAN, WAN, Internet network, etc.

If the unit 101 is a PC, workstation, intelligent device or the like, the software in the memory 110 may further include a basic input output system (BIOS). The BIOS is stored in ROM so that the BIOS can be executed when the computer 101 is activated.

When the unit 101 is in operation, the processor 105 is configured to execute software stored within the memory 110, to communicate data to and from the memory 110, and to generally control operations of the computer 101 pursuant to the software. The methods described herein and the OS 111, in whole or in part are read by the processor 105, typically buffered within the processor 105, and then executed. When the methods described herein are implemented in software, the methods can be stored on any computer readable medium, such as storage 120, for use by or in connection with any computer related system or method.

2.3 Computer Program Products

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access a normalized search engine or related data available in the cloud. For example, the normalized search engine could execute on a computing system in the cloud and execute normalized searches. In such a case, the normalized search engine could normalize a corpus of information and store an index of the normalizations at a storage location in the cloud. Doing so allows a user to access this information from any computing system attached to a network connected to the cloud (e.g., the Internet).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
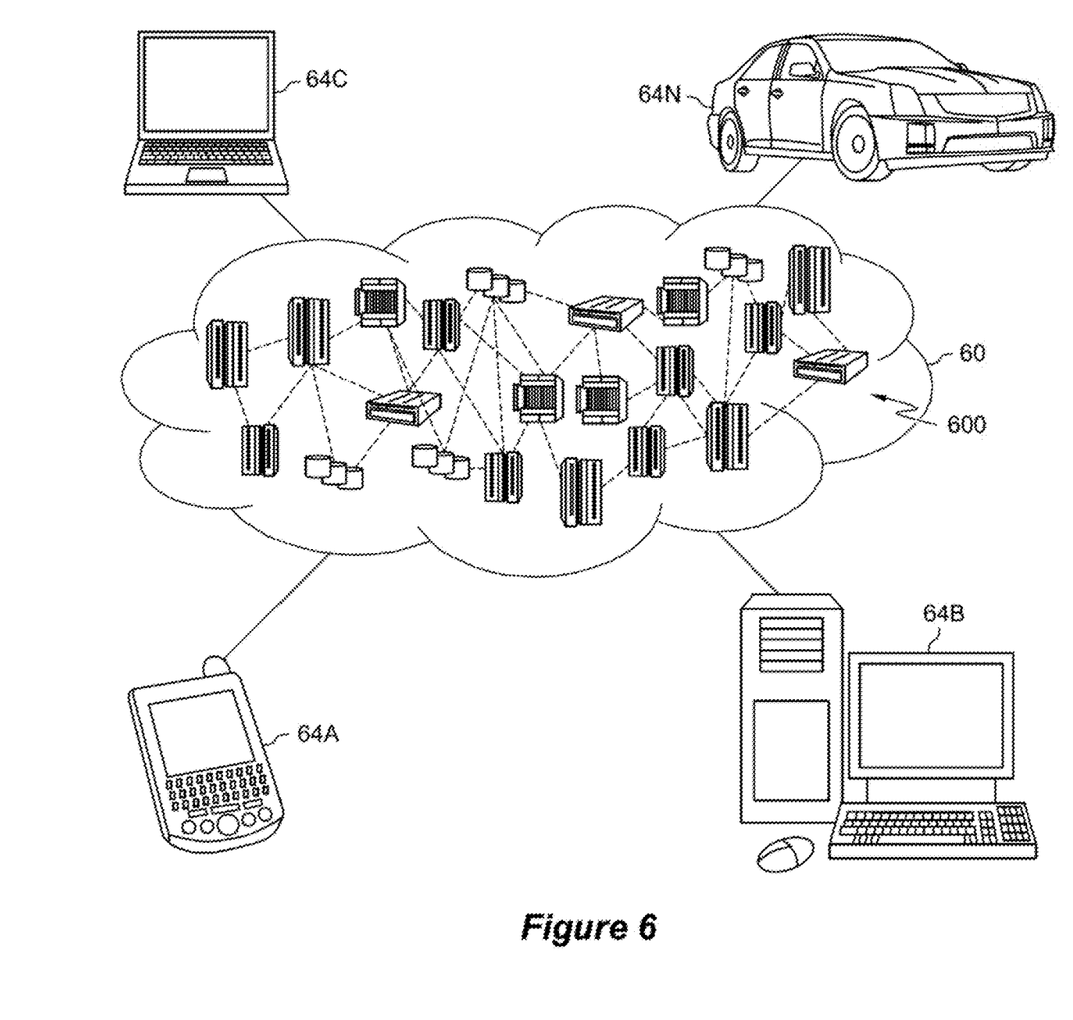
FIG. 6 depicts a cloud computing environment according to an embodiment of the present invention.

Referring now to FIG. 6, illustrative cloud computing environment 600 is depicted. As shown, cloud computing environment 600 includes one or more cloud computing nodes 610 with which local computing devices used by cloud consumers, such as, for example, personal digital assistant (PDA) or cellular telephone 640A, desktop computer 640B, laptop computer 640C, and/or automobile computer system 640N may communicate. Cloud computing nodes 610 may communicate with one another. They may be grouped (not shown) physically or virtually, in one or more networks, such as Private, Community, Public, or Hybrid clouds as described hereinabove, or a combination thereof. This allows cloud computing environment 600 to offer infrastructure, platforms and/or software as services for which a cloud consumer does not need to maintain resources on a local computing device. It is understood that the types of computing devices 640A-N shown in FIG. 6 are intended to be illustrative only and that cloud computing nodes 610 and cloud computing environment 600 can communicate with any type of computerized device over any type of network and/or network addressable connection (e.g., using a web browser).

Figure 7:
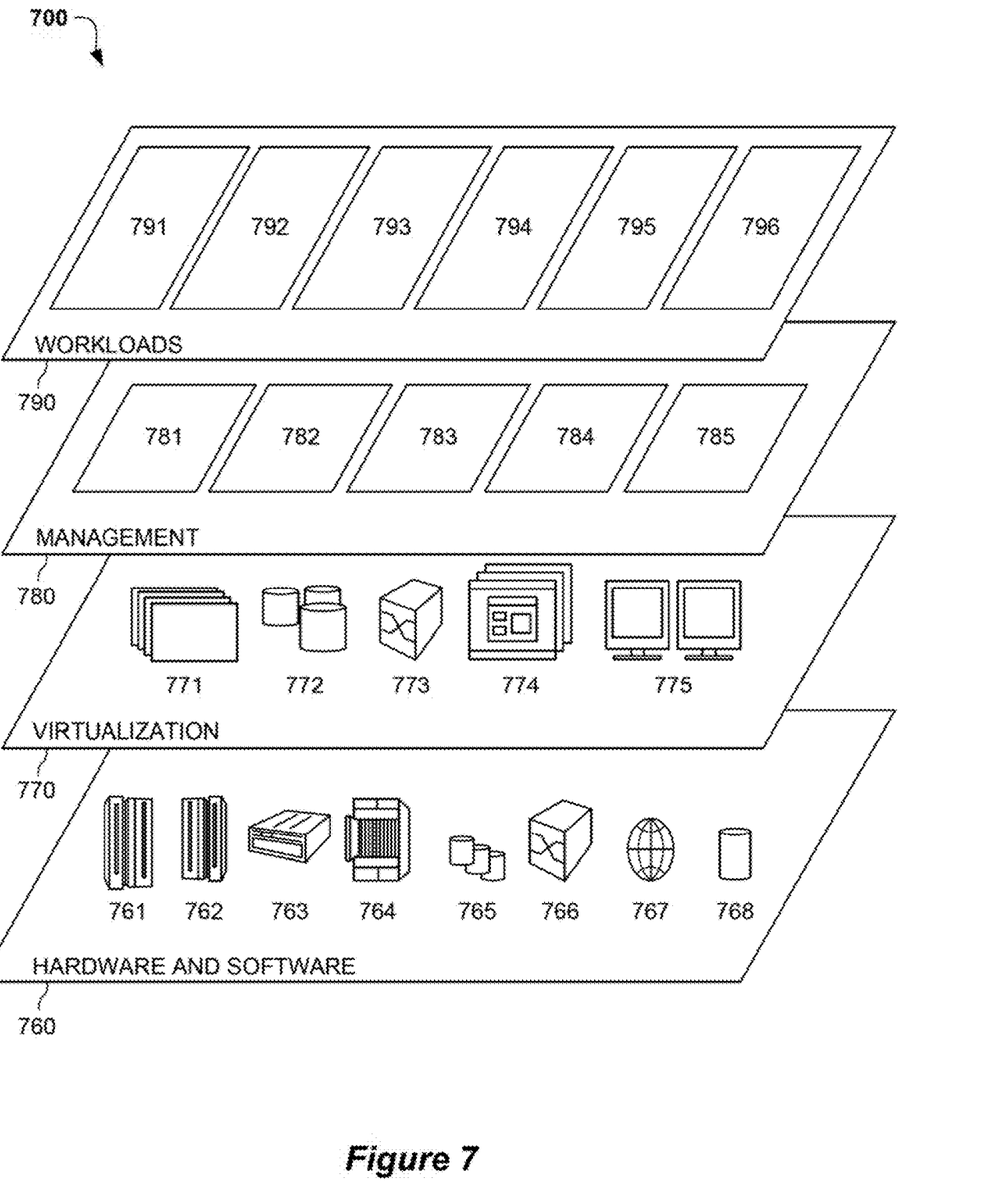

Referring now to FIG. 7, a set of functional abstraction layers provided by cloud computing environment 600 (as shown in FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772, for example the data storage device 120 as shown in FIG. 5; virtual networks 773, including virtual private networks; virtual applications and operating systems 774; and virtual clients 775.

In an example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In an example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 685 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and pre-processing whole slide program 796. The pre-processing whole slide program 796 preprocess whole slide images.

What is claimed is:

1. A computer-implemented method for normalizing medical images, wherein the method comprises, for each image of a first subset of images of a dataset:
   estimating actual quantities for each image, the actual quantities comprising actual stain vectors;
   assessing the actual quantities by comparing them to reference data, the reference data based on reference quantities estimated for one or more images of a second subset of images of the dataset, wherein the reference quantities include reference stain vectors, and wherein the second subset of images differ from the first subset of images;
   based on an outcome of assessing the actual quantities, selecting either the actual quantities or the reference quantities for the dataset as effective quantities; and
   based on the effective quantities selected; normalizing each image to obtain a normalized image.

2. The method according to claim 1, wherein
   the actual quantities estimated further include robust maximum stain concentrations and the reference quantities further include robust maximum reference stain concentrations, wherein each image is normalized based on both the actual stain vectors and the reference stain vectors, and the robust maximum stain concentrations of the effective quantities selected.

3. The method according to claim 2, further comprising:
   computing effective pixel stain concentrations of each image of the first subset based on effective stain vectors selected for each image, wherein each image is normalized based on both the effective pixel stain concentrations computed and the robust maximum stain concentrations of the effective quantities selected.

4. The method according to claim 2, wherein
   the actual stain vectors of each of the actual quantities and the reference quantities are vectors of hematoxylin and eosin,
   the actual stain vector of the actual quantities and the reference stain vector of t reference quantities are vectors of hematoxylin and eosin, and
   the robust maximum stain concentrations of each of the actual quantities and the reference quantities are robust maximum concentrations of hematoxylin and eosin.

5. The method according to claim 1, further comprising:
   estimating reference quantities for each of the one or more images of the second subset, and
   obtaining reference data based on the reference quantities estimated.

6. The method according to claim 4, wherein
   the reference quantities are estimated based on two or more images of the second subset.

7. The method according to claim 1, further comprising:
estimating all actual quantities for each image of the dataset, all quantities comprising actual quantities for images of the first subset, prior to assessing all quantities, comprising the actual quantities estimated for the first subset, in view of selecting the effective quantities for the images of the first subset.

8. The method according to claim 1, wherein
the reference data comprise the reference stain vectors, and
the actual quantities are assessed by measuring distances between the actual stain vectors and the reference stain vectors.

9. The method according to claim 8, wherein
the actual quantities are assessed by comparing the measured distance to a threshold di stance.

10. The method according to claim 1, wherein
the method further comprises, for each image, obtaining the reference data as boundary values for the actual quantities, based on the reference quantities; wherein the actual quantities are assessed by verifying whether values of the actual quantities estimated for each image lie outside of domains bounded by the boundary values and, if such values are verified to lie outside of the domains, then the reference quantities are selected as effective quantities for each image.

11. The method according to claim 1, wherein
the method further comprises updating metadata of the dataset based on outcomes of steps of assessing the actual quantities as estimated for each image.

12. The method according to claim 11, wherein
the metadata is updated to aggregate statistics as to whether the actual quantities as estimated for each image of the dataset have been selected as the effective quantities or not.

13. The method according to claim 11, further comprising:
for each image of a third subset of images of the dataset, the third subset of images being distinct from each of the first subset of images and the second subset of images;
loading the metadata; and
based on the loaded metadata, deciding whether to skip steps of estimating actual quantities and assessing actual quantities for each image of the third subset of images, or not, wherein the reference quantities are selected by default as effective quantities for normalizing each image of the third subset of images if it is decided to skip the steps.

14. The method according to claim 1, wherein
each image of the dataset is a whole slide image.

15. The method according to claim 1, wherein
each image of the dataset have been obtained according to a same staining process.

16. The method according to claim 1, wherein
the method further comprises running a cognitive algorithm based on normalized images as obtained from the dataset.

17. A computer system for normalizing medical images, the computer system comprising, for each image of a first subset of images of a dataset:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
estimating actual quantities for each image, the actual quantities comprising actual stain vectors;
assessing the actual quantities by comparing them to reference data, the reference data based on reference quantities estimated for one or more images of a second subset of images of the dataset, wherein the reference quantities include reference stain vectors, and wherein the second subset of images differ from the first subset of images;
based on an outcome of assessing the actual quantities, selecting either the actual quantities or the reference quantities for the dataset as effective quantities; and
based on the effective quantities selected, normalizing each image to obtain a normalized image.

18. The computer system according to claim 17, wherein
the actual quantities estimated further include robust maximum stain concentrations and the reference quantities further include robust maximum reference stain concentrations, wherein each image of the first subset of images is normalized based on both the stain vectors and the reference stain vectors, and the robust maximum stain concentrations of the effective quantities selected.

19. A computer program product for normalizing medical images, the computer program product comprising, for each image of a first subset of images of a dataset:
one or more computer-readable tangible storage medium and program instructions stored on at least one of the one or more tangible storage medium, the program instructions executable by a computing system to cause the computing system to perform a method comprising:
estimating actual quantities for each image the actual quantities comprising actual stain vectors;
assessing the actual quantities by comparing them to reference data, the reference data based on reference quantities estimated for one or more images of a second subset of images of the dataset, wherein the reference quantities include reference stain vectors, and wherein the second subset of images differ from the first subset of images;
based on an outcome of assessing the actual quantities, selecting either the actual quantities or the reference quantities for the dataset as effective quantities; and,
based on the effective quantities selected, normalizing each image to obtain a normalized image.

20. The computer program product according to claim 19, wherein
the actual quantities estimated further include robust maximum stain concentrations and the reference quantities further include robust maximum reference stain concentrations, wherein each of the first subset of images image is normalized based on both the stain vectors and the reference stain vectors, and the robust maximum stain concentrations of the effective quantities selected.

* * * * *